US008585796B1

(12) United States Patent
Fabry

(10) Patent No.: US 8,585,796 B1
(45) Date of Patent: *Nov. 19, 2013

(54) BACTERICIDAL AND FUNGICIDAL PHOSPHITE COMPOSITIONS AND RELATED METHODS

(76) Inventor: Carl Fabry, Zellwood, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/544,064

(22) Filed: Jul. 9, 2012

Related U.S. Application Data

(60) Continuation of application No. 13/308,681, filed on Dec. 1, 2011, now Pat. No. 8,221,516, and a division of application No. 13/019,564, filed on Feb. 2, 2011, now Pat. No. 8,088,191, and a division of application No. 11/349,064, filed on Feb. 6, 2006, now Pat. No. 7,887,616.

(60) Provisional application No. 60/650,378, filed on Feb. 4, 2005.

(51) Int. Cl.
*C05D 1/00* (2006.01)
*C05D 9/00* (2006.01)
*C01B 25/163* (2006.01)
*A01N 59/26* (2006.01)

(52) U.S. Cl.
USPC ............... 71/32; 71/33; 71/34; 71/41; 71/48; 423/307; 504/101

(58) Field of Classification Search
USPC ......... 423/307; 424/601; 504/101; 71/32, 33, 71/34, 36, 41, 48
See application file for complete search history.

(56) References Cited

U.S. PATENT DOCUMENTS

| | | | | |
|---|---|---|---|---|
| 7,887,616 | B1* | 2/2011 | Fabry | 71/32 |
| 8,088,191 | B1* | 1/2012 | Fabry | 71/32 |
| 8,221,516 | B1* | 7/2012 | Fabry | 71/32 |
| 2003/0029211 | A1* | 2/2003 | Sheppardson et al. | 71/33 |
| 2007/0166340 | A1* | 7/2007 | Stringfellow | 424/405 |

OTHER PUBLICATIONS

Lovatt, Carol "A Definite Test to Determine Whether Phosphite Fertilization Can Replace Phosphate Fertilization to Supply P in the Metabolism of Hass' on 'Duke 7' (A Preliminary Report)" 1990, Calidornia Avocado Society Yeasbook 74: p. 61-64.*

* cited by examiner

*Primary Examiner* — Wayne Langel
*Assistant Examiner* — Syed Iqbal
(74) *Attorney, Agent, or Firm* — Allen, Dyer, Doppelt, Milbrath & Gilchrist, P.A.

(57) ABSTRACT

A fertilizer composition comprising a phosphite ingredient that that is individually effective against both fungal and bacterial plant pathogens is disclosed. The fertilizer composition is useful as a fertilizer, fungicide, and bactericide when applied to plants. A method of making the fertilizer composition is also disclosed.

17 Claims, 5 Drawing Sheets

SAMPLE PFSO26, P31 NMR SPECTRUM        SAMPLE PFSO26, H1 TRANSFER POLARIZATION NMR SPECTRUM

SAMPLE PFSO30, P31 NMR SPECTRUM        SAMPLE PFSO30, H1 TRANSFER POLARIZATION NMR SPECTRUM

SAMPLE PFS 002
P³¹ NMR
BROAD PEAK:
CHARACTERISTIC OF
POLYMER

BACTERICIDAL AND FUNGICIDAL PHOSPHITE COMPOSITIONS AND RELATED METHODS

CROSS-REFERENCE TO RELATED APPLICATIONS

This application claims priority to and is a continuation of U.S. application Ser. No. 13/308,681 filed on Dec. 1, 2011, which is a division of U.S. application Ser. No. 13/019,564 filed on Feb. 2, 2011, now U.S. Pat. No. 8,088,191, which is a division of U.S. application Ser. No. 11/349,064 filed on Feb. 6, 2006, now U.S. Pat. No. 7,887,616, which claimed priority from U.S. provisional application Ser. No. 60/650,378, filed on Feb. 4, 2005. Each of these priority documents is incorporated herein by reference in its entirety.

FIELD OF THE INVENTION

The invention relates to the field of fertilizer compositions that can be used to treat both fungal and bacterial plant pathogens and, more particularly, to fertilizer compositions that include a phosphite ingredient that is individually effective against both fungal and bacterial plant pathogens.

BACKGROUND

Phosphorus-based fertilizers are one of three critical nutrients for agriculture around the world. The others are nitrogen and potassium. All important phosphorus-based fertilizers comprise phosphate, e.g. phosphate ion ($PO_4^{-3}$), and occasionally some proportion of polyphosphates, i.e. $P_2O_7^{-4}$, are included in the composition. Polyphosphates are ionic species formed by condensed phosphate ions ($PO_4^{-3}$) as illustrated in Formula 1.

$$2PO_4^{-3} + H_2O \rightarrow P_2O_7^{-4} + 2OH^- \qquad \text{Formula 1}$$

Polyphosphates are sometimes referred to as pyrophosphates. Additional phosphate ions may react further with the polyphosphate, $P_2O_7^{-4}$, to form longer polyphosphates and, in general, there is a mixture of varying polymer chain lengths in any given sample. The presence of some proportion of polyphosphates in a fertilizer is useful for purposes of sequestration of impurities, as suspensions aids, and for making phosphorus more available to plants.

U.S. Pat. No. 3,917,475 describes a process for the preparation of a fertilizer containing a significant amount of polyphosphate. Formation of polyphosphate is favored by high concentrations of reactants and by high reaction temperatures, followed by rapid cooling. However, at high temperatures, the chemical bonds in polyphosphate can hydrolyze to yield the starting phosphate ion, ($PO_4^{-3}$) and acid, as shown in Formula 2 (taken from *Western Fertilizer Handbook*, Interstate Publishers, Inc., Danville, Ill., Eighth ed., p 148, 1985).

$$P_2O_7^{-4} + H_2O \rightarrow 2PO_4^{-3} + 2H^+ \qquad \text{Formula 2}$$

On the other hand, the lower valent phosphite, ($PO_3^{-3}$), has never played an important role in the commercial fertilizer industry.

A few academic research papers have been published describing alkali metal and organic esters of polyphosphites. For instance, Payne and Skledar of the University of Glaskow in *J. Inorg. Nucl. Chem.*, 1964, Vol. 26, pp 2103-2111 describe the preparation of "pyrophosphates" by thermal decomposition of alkali metal phosphites. An academic paper from Russia in 1970 (CA 76:71456) describes a method of preparing ammonium polyphosphite by starting with phosphorous acid that has already been polymerized and reacting it with ammonia under pressure and at high temperature. Using polyphosphorous acid as a reactant to produce polyphosphites, however, is not economically feasible for commercial production.

The analysis of polyphosphite content in a composition is difficult because common wet chemical methods for determination of phosphite depend upon reagents that first convert phosphite to phosphate. These reagents will break up any polyphosphite molecules present in the composition into individual phosphite ions. Polyphosphite, therefore, cannot be detected or quantified by the routine wet chemical methods. For instance, iodine solutions are used to oxidize inorganic phosphites for subsequent analysis as phosphate. Iodine will breakup any phosphite polymer present and the polyphosphite will not be detected.

Similarly, commercial labs which analyze fertilizers do not report phosphite levels but rather report them as phosphate. Also, during analytical procedures requiring heat, phosphites would typically be slowly converted to phosphate unless precautions are taken to prevent oxidation by excluding air. Furthermore, at elevated temperatures polyphosphites can be expected to hydrolyze to ordinary phosphite ion, analogously to the hydrolysis of polyphosphates under similar conditions. Accordingly, physical methods such as nuclear magnetic resonance (NMR), high pressure liquid chromatography (HPLC), liquid chromatography, mass spectrometry (MS), and other physical molecular weight determining methods are useful methods for characterizing polyphosphites.

NMR provides a unique method of detecting phosphite because in most cases, and particularly when in solution, it exists with a hydrogen attached to the phosphorus atom ($HPO_3^{-2}$). Sophisticated NMR instruments, such as the Varian VXR-300S spectrometer, can not only detect and measure $P^{31}$ but can also simultaneously perform measurements on atoms such as hydrogen attached to phosphorus or carbon by transfer polarization. Such an instrument can, therefore, detect and measure phosphite in the presence of other phosphorus species without ambiguity.

Inorganic phosphite compositions such as potassium phosphite are known to be useful as fungicides, as described in U.S. Pat. Nos. 5,736,164, 5,800,837, and U.S. 2003/0029211A1, for instance. As is common with all commercial chemicals, however, and particularly so with environmentally sensitive chemicals such as fungicides, less is often better. Therefore, there is always a need for enhanced performance at an equivalent dose.

In this context, potassium phosphite would be particularly useful because it would provide the second important nutrient of the three critical plant nutrients, potassium. Moreover, a polyphosphite can be expected to provide the sequestration and slow release advantages known with polyphosphate, although phosphites are more active fungicides.

Currently available commercial methods for preparation of fertilizer grade potassium phosphite, $KH_2PO_3$ and/or $K_2HPO_3$, are carried out by charging an aqueous potassium hydroxide solution to a mixing tank equipped with an agitator and with cooling means (commonly called a batch reactor). Alternatively, potassium carbonate could be used as a reactant instead of potassium hydroxide. Phosphorous acid is added to the potassium hydroxide, slowly at first, then more rapidly toward the end of the reaction. This process is subject to a number of problems.

The reaction can be violent and on a large scale, even with good agitation and cooling, the reaction can run away explosively. In fact, at least two fatalities and numerous injuries have resulted recently from such run away reactions. During the early addition of phosphorous acid, even if the reaction does not run away, localized excessive heat release occurs, even when the overall temperature is at or below 200° F. Furthermore, it is known in the art that hazardous toxic phosphine gas, which has a characteristic garlic-like odor, may be emitted during the reaction when the temperature reaches 150° F., which creates a hazard unless properly absorbed. In addition, a batch reactor is difficult to seal and prevent oxygen in the air from entering, which readily oxidizes the phosphorous acid to phosphoric acid, preventing formation of phosphites.

The necessary slow addition of the acid results in the hydroxide always being in excess until close to the end of the reaction, thus hindering formation of the desired polyphosphite. As a consequence, and also due to low temperatures, previous processes can be expected to provide little or no formation of polyphosphites.

Yet another potential problem which occurs in batch processes is poor control of the addition rate of and total quantity of reactants present in the mixture. Extra care must be taken in measuring ingredients and in the rate of addition which is time consuming and labor intensive. Lack of attention by the technician can lead to an explosive run away reaction.

U.S. Pat. No. 3,585,020 by Legal, Jr., et al. describes a process for forming a free-flowing, granular, non-burning and non-crumbling 7-40-6 fertilizer composition. Reference is made at column 3 to the use of an inline mixer. However, the use of spargers in the process suggests that it is specific to batch processing. In any case, the reference by Legal, Jr., et al. is specific to forming granular materials quite different from the liquid solutions prepared in the invention.

In U.S. Pat. No. 3,957,947 Yamada et al. describe a process for the continuous production of aqueous basic aluminum salt solutions. The products of Yamada appear to be deodorants, and while a short tubular reactor is involved, it is necessary to provide heat on an indirect basis and the overall reaction scheme is quite different from that of the invention.

The Environmental Protection Agency, classifies potassium phosphite compositions as "biopesticides" under their regulatory classification, for reduced registration requirements. As such, the active ingredient, mono- and di-potassium salts of phosphorous acid are synthesized active ingredients involving a mixed mode of action by direct toxicity to plant pathogens, and by activating the plants natural defense mechanisms, in disease suppression or elimination.

Potassium phosphites are systemically absorbed by the plant and are mobile within the plant, translocating to the new growth via both the phloem and the xylem. They are rapidly absorbed by the leaf tissue and roots for maximum and efficient plant use by moving systemically upward and downward in the plants vascular system, including the root system. The mode of action is thought to be two-fold, first acting within the fungus by "walling off" the pathogen, killing off surrounding cells when attacked by disease or insects, and inhibiting further fungus growth. This is observed as yellowing around a diseased area. Secondly, the plant then responds further by activating the plant's own immune self-defense system, through rapid cytological action, and triggering other cellular phytoalexin accumulations and metabolic changes and other resistance inducers. Various chemical compounds are released that alert the rest of the plant to begin producing other compounds that increase plant resistance to infection or attack at other sites on the plant. These two types of responses are known as systemic acquired resistance (SAR) and induced resistance (IR).

As a result, phosphites are highly selective, non-toxic fungicides active against numerous fungal pathogens, and provide both protective and curative responses against such plant disease isolates of *Phytophthora, Rhizoctonia, Pythium*, and *Fusarium*, and other plant diseases—but typically not against bacterial diseases.

The extreme difficulty, or even the total lack of bacterial disease control, by induced systemic resistance compounds, including those based on the salts of phosphorous acid, and particularly the potassium salts, is well known. For example, the benchmark product, "Aliette", a product comprising aluminum salts of phosphorous acid and EPA-registered pesticide, does not provide for any bacterial disease control.

SUMMARY

In view of the foregoing, it is an object of the invention to provide fertilizer compositions, methods of making a fertilizer composition and methods of using fertilizer compositions, wherein the fertilizer compositions comprises a first phosphite compound that is individually effective against both fungal and bacterial plant pathogens. An exemplary phosphite compound is a polyphosphite, such as, for example, potassium polyphosphite. In some embodiments in which potassium polyphosphite is used, the concentration of the potassium polyphosphite is approximately 25-75% by weight of the fertilizer composition.

In some embodiments, the fertilizer composition comprises a second phosphite compound, the second phosphite having a lower molecular weight than the first phosphite compound. In such embodiments, the first phosphite compound may be a polyphosphite and the second phosphite compound may be potassium phosphite, the polyphosphite being approximately 25-75% by weight of the fertilizer composition.

In some embodiments, the fertilizer compound comprises the first phosphite compound and one or more of potassium phosphate, potassium polyphosphate, and potassium phosphite.

In a method aspect of the invention, a method of making a fertilizer composition comprises heating phosphorous acid and potassium hydroxide in an aqueous solution at a temperature sufficient to form a first phosphite compound, wherein the first phosphite compound is individually effective against both fungal and bacterial plant pathogens and allowing the solution to cool. Preferred temperatures are at least approximately 260° F., approximately 270° F. to approximately 285° F., or approximately 260° F. to approximately 275° F. An exemplary phosphite compound is a polyphosphite, such as, for example, potassium polyphosphite. In some embodiments in which potassium polyphosphite is produced by the method, the concentration of the potassium polyphosphite is approximately 25-75% by weight of the fertilizer composition.

In some embodiments, the temperature is sufficient to form a second phosphite compound in combination with the first phosphite compound, the molecular weight of the second phosphite compound being less than the molecular weight of the first phosphite compound. Examples of second phosphite compounds having lower molecular weights than the first phosphite compound are phosphite salts such as potassium phosphite.

In some embodiments, the temperature is sufficient to form both the first phosphite compound and one or more of potassium phosphate, potassium polyphosphate, and potassium phosphite.

In another method aspect of the invention, a method of treating a plant for a bacterial or fungal infection comprises applying an effective amount of a fertilizer composition comprising a phosphite compound that is individually effective against both fungal and bacterial plant pathogens to a plant. An exemplary phosphite compound is a polyphosphite, such as, for example, potassium polyphosphite. In some embodiments in which potassium polyphosphite is used, the concentration of the potassium polyphosphite is approximately 25-75% by weight of the fertilizer composition.

These and other objects, aspects, and advantages of the invention will be better appreciated in view of the drawings and following detailed description of the preferred embodiments.

BRIEF DESCRIPTION OF THE DRAWINGS

Some of the features, advantages, and benefits of the invention having been stated, others will become apparent as the description proceeds when taken in conjunction with the accompanying drawings, presented for solely for exemplary purposes and not with intent to limit the invention thereto, and in which.

DETAILED DESCRIPTION OF PREFERRED EMBODIMENTS

The invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Figure 1:
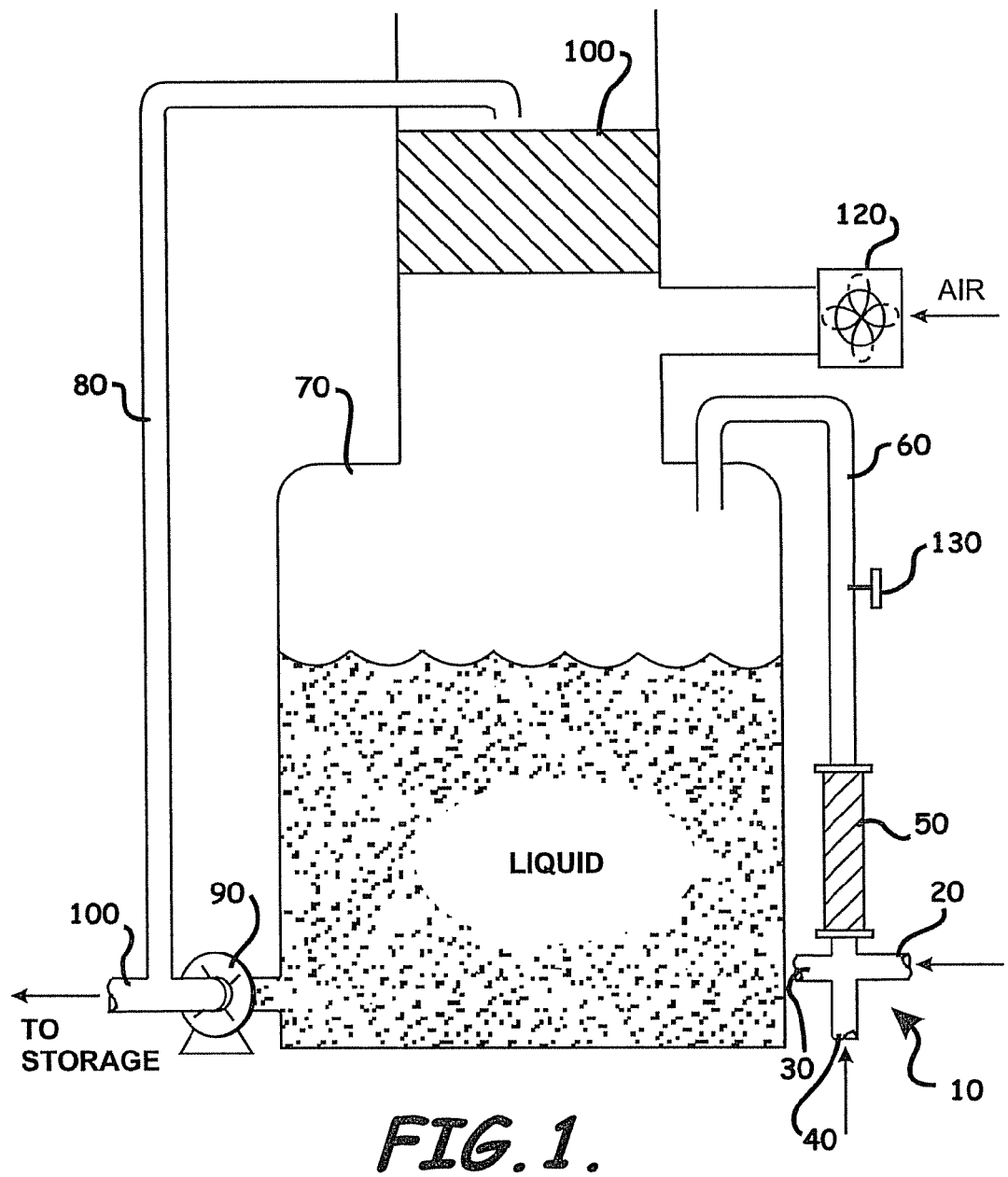
FIG. 1 is a cross-sectional side elevation view of an apparatus which may be used in preparing the compositions according to an embodiment of the invention.

A preferred embodiment of the invention employs the cross-pipe reactor described in U.S. Pat. No. 4,724,132 (the '132 patent) in combination with a down-stream mixer which is a static in-line mixer, the static in-line mixer can be extremely short or, in fact, the static inline mixer could comprise the entire length of the pipe 60 as shown, in which case the static in-line mixer would essentially deliver product into receiving tank 70 and FIG. 1 would be modified to basically delete pipe 60. The primary criterion which would set the length of the static in-line mixer, if it is used, is to insure that reaction is substantially complete prior to the time the product enters the receiving tank 70 as shown in FIG. 1. Generally speaking, if the static in-line mixer (or some other mixer) is not used downstream the cross-pipe reactor the length of the pipe 60 should be increased to insure substantially complete reaction with a decrease in the length of pipe 60 if a static in-line mixer is used. The exact length of the static in-line mixer and/or the pipe 60 can easily be determined by standard chemical engineering practices.

The excellent mixing, polymerization and temperature obtained with the cross-pipe reactor creates a greater potassium hydroxide solution/acidulation surface area, and insures good conversion of the potassium compound(s) to polyphosphite salt. Acidulation is, of course, the process of adding acid, and generally the amount of mineral acid, phosphorous acid, is specified with respect to the amount of potassium hydroxide. This can easily be established by one skilled in the art.

As indicated, even more pronounced effects are obtained with the addition of a static in-line mixer down-stream from the cross-pipe reactor. A typical static in-line mixer useful in the invention and, in fact, the one that has been used to date, is disclosed in U.S. Pat. No. 4,093,188 Horner, hereby incorporated by reference. The particular static in-line mixer disclosed has stationary baffles providing sinuous, non-parallel spiraling flow paths to promote thorough and homogeneous intermixing of fluids. It is not mandatory to use that precise static in-line mixer and other static in-line mixers, also known as stationary baffle mixers or interfacial surface generators, can be used. For example, it is believed that stationary baffle mixers or interfacial surface generators as disclosed in U.S. Pat. Nos. 3,190,618; 3,620,506; 3,643,927; 3,652,061; 3,923,288; 3,947,939 and Reissue No. 28,072 could be used with equal success, and all of these patents are also incorporated by reference. Other mixers could likely be used instead of a static in-line mixer, for example, as can be appropriately selected by one skilled in the art from the Chemical Engineers' Handbook, John H. Perry, Editor, Third Edition, McGraw-Hill Book Co., Inc., pp. 1195-1231.

After the reactants have passed through the cross-pipe reactor 10, the mixer 50 and pipe 60, the reacted mixture is conveniently discharged into a receiving tank 70. Generally, it is preferable to substantially complete reaction prior to introduction of the product into the receiving tank 70. As one skilled in reaction kinetics will appreciate, there will be some slight amount of reaction in the receiving tank 70, but this is not of consequence if any reasonable amount of care is exercised over process control, as would be understood by a chemical engineer. The discharge is usually above the level of the liquid in the receiving tank 70 in order to achieve faster flash cooling. If the discharge is below the liquid level, reducing to some degree the cooling capacity, the conversion ratio from metal hydroxide solution to salt is slightly improved. As will be appreciated by one skilled in the art, the use of a receiving tank is merely a convenient means to use a cool, large mass of product to inexpensively cool the product received from pipe 60. The composition should be cooled to approximately 90° F., or less, as rapidly as possible. Any conventional means could be used to achieve this cooling effect.

The determination and adjustment of optimum reaction parameters will be well within the skill of the chemical engineer. The product can be recirculated from receiving tank 70 through cooling means (not shown) via pump 90. If desired, some product can be sent to storage via line 100 but normally the greater volume is recirculated over a packed column 110 through which air is blown by fan 120 in order to cool the product prior to storage. Also, as one skilled in the art will appreciate, pumping means are provided throughout the system as needed; these are conventional and are not shown. Further, the skilled will recognize that, since a mineral acid is being used, conventional process equipment resistant to acidic conditions will be used, typically stainless steel.

Figure 2:
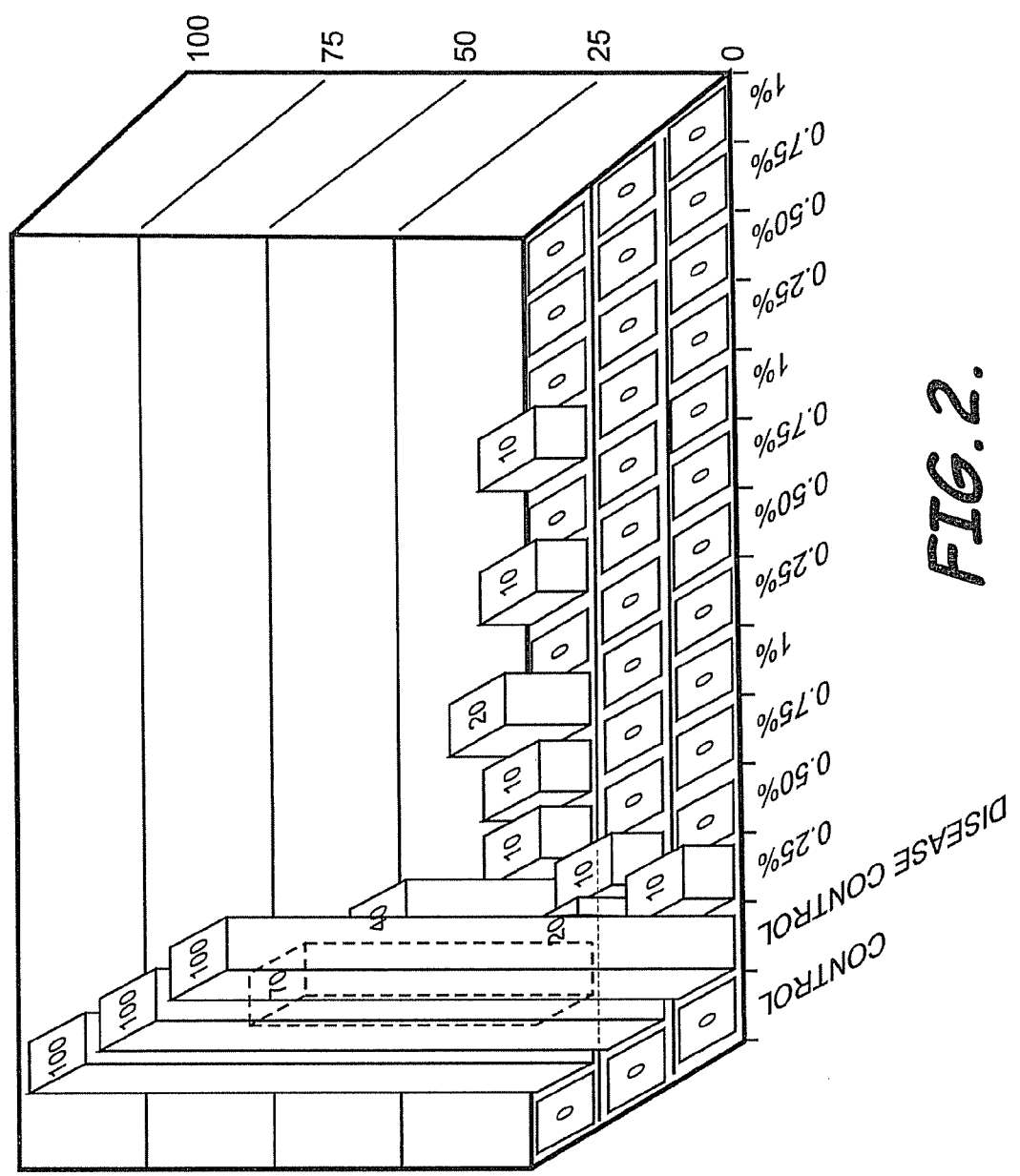
FIG. 2 is a graph showing activity of the present polyphosphite composition against some bacterial agents of plant disease.

Evidence of the makeup of the composition is found in NMR results of several samples and from chemical tests. Samples were prepared by the use of the apparatus of the invention as shown in FIG. 1 and described below. NMR analysis was conducted by Process NMR Associates, LLC, using a Varian VXR-300S Spectrometer. Spectra were recorded and the position of the peaks noted in terms of parts per million of field strength (ppm) relative to the standard inorganic phosphate peak. Simultaneously, the samples were examined for the hydrogen atom attached to the phosphorus atom using the transfer polarization technique. Concentration, different counter-ions, such as ammonium, sodium, or potassium can cause a small change in position of the peaks, therefore the exact position of the peaks in a given spectrum is not definitive. However, the relative position of one peak to another, such as phosphate versus phosphite, is useful. Potassium phosphite alone exhibits a single sharp peak for the $P^{31}$ atom and a correspondingly sharp peak in the transfer polarization spectrum for the $H^1$ atom that is attached to the P atom of all inorganic phosphites. To the contrary, no corresponding transfer polarization spectrum for $H^1$ is found for polyphosphites, which clearly indicates that there are no longer $H^1$ atoms attached to the phosphorus and that the starting material, $HPO_3^{-2}$, has been chemically changed. In addition, in confirmation of polymeric character, the peak is no longer sharp (half width of about 10 to 20 Hz) but very broad (half width of about 30 to 100 Hz). The breadth of such $P^{31}$ NMR peaks, at a given field strength, is the result of the different positions of phosphorus atoms in the polymer and the different molecular weights of oligomers. Accordingly, each atom yields a signal indicating its unique environment and, since the signals are only slightly different, the result is a broader peak. In the case of phosphite and polyphosphite, the peak positions are very near each other and a broad peak can cover a smaller narrower peak. Under the different conditions in the various examples of the invention, the composition prepared may contain more or less potassium polyphosphite with the balance being simple potassium phosphite. However, several samples have been prepared by this invention that give no detectable response for $P^{31}$—$H^1$ in transfer polarization NMR analyses, thereby indicating that the samples are nearly 100% polymerized $PO_3^{-3}$, polyphosphite. Furthermore and analogous to polyphosphate chemistry, it has been found that the composition prepared by the invention readily generates free acid when they are heated above ambient temperature thereby providing further confirmation of the proposed structure, as illustrated in FIG. 2. The amount of free acid continues to increase with time as the composition is held at an elevated temperature.

A most preferred embodiment in a continuous process of the invention will be described with reference to the FIG. 1 and comprises a metal hydroxide solution, e.g., potassium hydroxide solution, as an aqueous solution reacted with a mineral acid, e.g., phosphorous acid, with water being added as necessary to adjust specific gravity. The metal hydroxide solution is pumped into port 20 of the cross-pipe tee 10, the mineral acid is pumped to port 30 and the water is pumped into port 40. Reaction begins on contact of the metal hydroxide solution and mineral acid and the mixture of the reactants is forced substantially immediately into the static in-line mixer 50 where reaction continues to occur. The rate of total feed is controlled so that the temperature as taken about midway up the pipe 60 above the in-line mixer 50 is maintained at a desired level, and preferably at about 300° F.+/− 50°. Generally speaking, the reaction continues in the pipe 60. Since the reaction of the invention is exothermic, external heat need not be supplied to the system. As a general practice, I simply measure the temperature about one-half way up the distance of the pipe 60 as shown in the FIG. 1 by temperature indicator 130. However, the temperature could easily be measured anywhere between the cross-pipe reactor and discharge into the receiving tank 70 as shown in FIG. 1. The ratio of the potassium hydroxide solution to phosphorous acid fed is adjusted to maintain product pH specification at the desired level, depending on the type of product being manufactured. The rate of water addition is controlled to maintain the desired product specific gravity. Product specific gravity is a relatively precise number and is typically set by the tolerances of fertilizer control laws. It can be freely selected by one skilled in the art. Various examples follow, including one example of a prior art batch process which is inadequate for use in the invention.

Example 1

This example is a batch process and represents prior art methods, rather than a method of the invention. It is presented here to show how the prior art is unable to achieve the results provided by the invention.

Into a 5,000 ml stainless steel laboratory blend tank outfitted with an electric driven propeller-type mixer, a 2,000 gram batch of a 70% solution of phosphorous acid was dissolved and prepared from 1,414 grams of 99% white, crystalline phosphorous acid, into 586 grams of distilled water. A 70% solution of phosphorous acid is the normal concentration commercially available that is typically used in the production of phosphorous acid products. Heat was applied in order to keep the temperature at 70° F. throughout the process and the mixture was stirred vigorously for approximately 10 minutes to obtain a uniform, clear solution of phosphorous acid. This solution was then poured off into a flask and stoppered. Of this solution, 918 grams was weighed into another flask and stoppered. 1,239 grams of 50% KOH was weighed and stored in a separate flask, both weighed products being of sufficient quantity in order to blend a 2,000 gram batch of a typical potassium phosphite product by the batch method, as known by those practicing in the art. There was a negative −157 gram imbalance of water which was expected to evaporate off as a result of the exothermic reaction. The 1,239 grams of KOH was poured into the above described 5,000 ml tank, and agitation begun. At this point the laboratory ventilation system should be engaged and the technician should wear proper laboratory safety attire, including goggles, for handling hazardous materials. Then, the addition of the 918 grams of acid was started with continuous agitation. The rate of addition of acid was maintained as fast as possible but without causing vigorous boiling of the water. During addition of the first 200 grams of acid, the batch began to boil vigorously, with the temperature reaching about 150° F. Upon cooling sufficiently, another 200 grams of acid was added slowly to the boiling point again continuously from the mixture. When most of the calculated amount of acid had been added, a very faint garlic-like odor was detectable, indicative of the formation of phosphine. The lab was immediately vacated until it was determined that the mixture had stopped boiling and that the lab had been properly ventilated. Personnel reentering the lab donned protective masks. It was not possible to complete the batch without exceeding about 130° F., without the material boiling over and out of the tank, and without the further risk of producing phosphine gas. The final pH was adjusted to 6.8 and the mixture was cooled in a water bath.

Example 2

This example describes the general process employed in the invention, in the temperature range as used also in examples 4 and 6. A run was carried out using equipment as shown in the above describe crosspipe reactor and including a special mixing device, i.e., an open cross-pipe reactor with a static in-line mixer. As disclosed in U.S. Pat. No. 4,093,188 Horner. It is commercially available under the trade name STATA-TUBE and is a motionless mixture manufactured by TAH Industries, P.O. Box 178, Imlaystown, N.J. 08526, (2" L.D. times.96" length). In the Examples herein the runs were on a commercial scale using a cross tee reactor where the ports had an inner diameter of about 2 inches" and the pipe was about 96" in length having an inner diameter the same as the cross tee reactor ports. Obviously these dimensions are not restrictive and smaller and/or larger devices can be used. All process lines were stainless steel. Reactants were pumped into the cross-pipe injection ports as follows: a 50% solution of potassium hydroxide at a rate of approximately 21 gallons per minute (port 20), and 70% phosphorous acid at a rate of 15 gallons per minute (port 30). Water at a rate of approximately 3 gallons per minute was injected directly into the receiving tank, in order to attain the highest pipe temperature possible. The reaction product was simply flowed into a receiving tank above the liquid level for ease of operation. During the run frequent samples were taken from the tank for pH and specific gravity checks, and acid and water flows were adjusted to maintain these values at the desired levels, i.e., pH 6.8, specific gravity 1.45 (these values are the same in the following Examples unless indicated to the contrary). Acidulation and conversion were thus controlled. During the run the temperature at the midpoint of the pipe fluctuated from 260° F. to 275° F. The reactionary product entering the receiving tank was instantly cooled to about 115° F. and was pumped to a finished product storage tank at a rate of approximately 33 gallons per minute. As a result of the evaporative cooling process taking place, voluminous steam plume was continuously emitted, and sampled for any trace of a garlic like odor, and none was detected.

Example 3

Using the process of Example 2, the reactants were introduced at lower rates, sufficient to keep the temperature at the midpoint of the pipe below 200° F. and a small portion of the resulting composition was immediately brought into the laboratory and packaged for rapid shipment to NMR Associates, LLC in Connecticut for testing by NMR. The NMR analysis revealed strong narrow peaks both for $P^{31}$ and $H^1$, which is indicative of the presence of the inorganic salt potassium phosphite.

Example 4

A run was carried out using the process of Example 2 where the temperature at the midpoint of the pipe was between 260° F. and 275° F. and a small portion was immediately brought into the laboratory and packaged for rapid shipment to NMR Associates, LLC in Connecticut for NMR analyses. The NMR analysis revealed a single broad strong peak for $P^{31}$ and only small evidence of $H^1$ attached to $P^{31}$ under the polarization transfer test, which indicates that most of the inorganic potassium phosphite had been converted to polyphosphites but that some monophosphite remained.

Example 5

Figure 5:
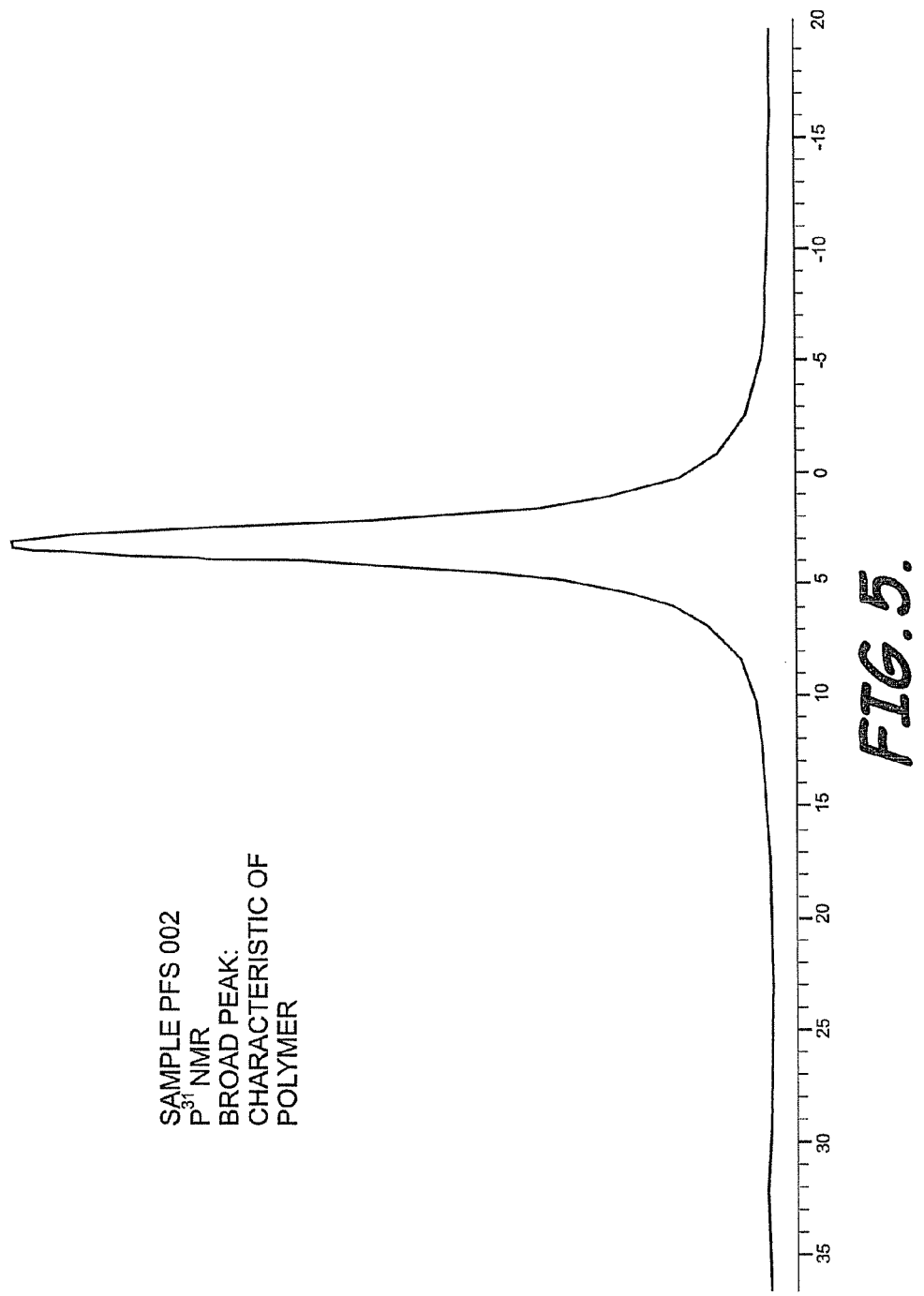
FIG. 5 shows a NMR spectrum for $P^{31}$ for sample PFS 002, as described in Example 5.
Figure 6:
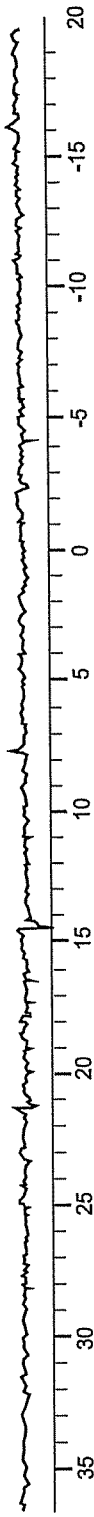
FIG. 6 is a NMR $H^1$ polarization transfer spectrum also for sample PFS 002.

The process of Example 2 was followed, where the temperature at the midpoint of the pipe was maintained between about 270° F. and 285° F. A small portion was immediately brought into the laboratory and packaged for rapid shipment to NMR Associates, LLC in Connecticut for NMR analyses; this was labeled sample PFS 002. As shown in FIGS. 5-6, the NMR analysis revealed a single broad strong peak for $P^{31}$ but no evidence of $H^1$ attached to $P^{31}$ under the polarization transfer. This result indicates that essentially all of the inorganic potassium phosphite had been converted to polyphosphites.

Example 6

The process of Example 2 was carried out, but where the temperature at the midpoint of the pipe was maintained between about 260° F. and 275° F. Eight days later, a five-gallon sample was taken from the storage tank and portions were subjected to heat treatment at various temperatures as follows. The sample had a specific gravity of 1.46, a pH of 6.5, and the dry solids content was about 53%. The NMR showed a large narrow peak for $P^{31}$ and also a significant peak for $H^1$ under transfer polarization. A portion, 232 g, was heated over a period of 13 minutes in an open stainless steel pan until it boiled at 116° C. Weight measurements showed a loss of 53 g of water. Further heating for a period of 15 minutes resulted in an additional loss of water of 33 g and the boiling point climbed to 145° C. The pH was 3. Another portion of 223 g of the original sample was heated in a similar manner but for less time so that the solution remained homogeneous. The pH was 4.

These experiments showed that free acid was being liberated upon heating, which is to be expected when hydrolysis of polyphosphite occurs. These data are consistent, indicating a sample containing a mixture of potassium phosphite (monomer) and polyphosphites.

Example 7

A mixture of phosphoric acid and phosphorous acid was prepared for use in the reactor of the invention. Five hundred pounds (500 lb) of solid 99% phosphorous acid was dissolved in 1500 lb of 75% phosphoric acid in order to increase the concentration of reactants by reducing the amount of water, and so as to subsequently increase the reaction temperature. This acid mixture was reacted with a 50% solution of potassium hydroxide, the reaction expected to yield a mixture of potassium phosphate and potassium phosphite. The test run lasted approximately 3 hours.

Figure 3:
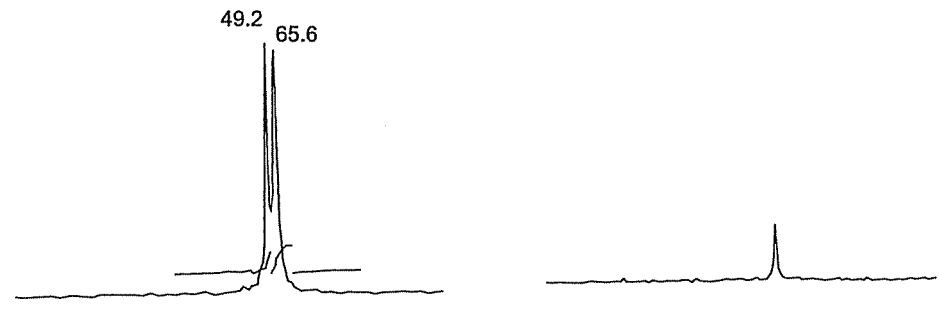
FIG. 3 shows NMR spectra for sample PFS 026, as described in Example 7.

The conditions of the reaction were varied over this period of time in order to study the effect of operational parameters. Five different conditions were studied. A small sample (7A) was withdrawn after each change in the reaction conditions after the system had stabilized. Sample number PFS026 was obtained when the reaction temperature was about 265° F., the pH was 8.22, the specific gravity was 1.475, and the sample temperature was 105° F. The NMR spectra for this sample are shown in FIG. 3. The $P^{31}$ spectrum shows two sharp peaks indicative of potassium phosphate and potassium phosphite. The H[1] spectrum for the hydrogen attached to the phosphorus atom, obtained by polarization transfer, confirms the presence potassium phosphite as expected.

Figure 4:
FIG. 4 shows NMR spectra for sample PFS 030, as described in example 7.

Sample PFS030 (7B) was obtained when the reaction temperature was about 300° F., the pH was 7.6, the specific gravity was 1.44, and the sample temperature was 100° F. The NMR spectra are shown in FIG. 4. Surprisingly, the P[31] spectrum shows a very broad peak consistent with formation of polymer. The spectrum also shows small peaks at the top of the broad peak indicative of small amounts of unreacted potassium phosphate and potassium phosphite. Also surprisingly, the H[1] polarization transfer spectrum shows an absence of hydrogen atoms attached to the phosphorus atom and which clearly indicates that an unexpected chemical reaction has resulted in almost complete polymer formation.

The results obtained in the examples set out above are also shown in TABLE 1, below, for easy comparison.

TABLE 1

| SAMPLE | TEMP (F.) | PHOSPHINE | MONO PO$_3$ | POLY PO$_3$ |
|---|---|---|---|---|
| EX. 1 (batch) | ≤150° | YES | N/A | N/A |
| EX. 2 | 260-275° | NO | N/A | N/A |
| EX. 3 | <200° | NO | YES | NO |
| EX. 4 | 260-275° | NO | YES | YES |
| EX. 5 | 270-285° | NO | NO | YES |
| EX. 6 | 260-275° | NO | YES | YES |
| EX. 7A | ~265° | NO | YES | YES |
| EX. 7B | ~300° | NO | NO | YES |

Accordingly, in the drawings and specification, there have been disclosed typical preferred embodiments of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed is:

1. A fertilizer composition comprising a polyphosphite compound that is individually effective against both fungal and bacterial plant pathogens.

2. The fertilizer composition of claim 1, wherein the polyphosphite is potassium polyphosphite.

3. The fertilizer composition of claim 2, wherein a concentration of the potassium polyphosphite is approximately 25-75% by weight of the fertilizer composition.

4. The fertilizer composition of claim 1, further comprising a second phosphite compound having a lower molecular weight than the polyphosphite compound.

5. The fertilizer composition of claim 4, wherein the polyphosphite compound is potassium polyphosphite and the second phosphite compound is potassium phosphite, the potassium polyphosphite being approximately 25-75% by weight of the fertilizer composition.

6. The fertilizer composition of claim 1, further comprising one or more members selected from the group consisting of potassium phosphate, potassium polyphosphate, and potassium phosphite.

7. A method of making a fertilizer composition, the method comprising:
heating phosphorous acid and potassium hydroxide in an aqueous solution at a temperature sufficient to form a polyphosphite compound individually effective against both fungal and bacterial plant pathogens; and
allowing the solution to cool.

8. The method of claim 7, wherein the temperature is at least approximately 260° F.

9. The method of claim 7, wherein the temperature is approximately 270 to approximately 285° F.

10. The method of claim 7, wherein the polyphosphite is potassium polyphosphite.

11. The method of claim 10, wherein the temperature is sufficient to form a second phosphite compound in combination with the polyphosphite compound, the molecular weight of the second phosphite compound being less than the molecular weight of the polyphosphite compound.

12. The method of claim 11, wherein the first polyphosphite compound is potassium polyphosphite and the second phosphite compound is potassium phosphite.

13. The method of claim 12, wherein the temperature is approximately 260° F. to approximately 275° F.

14. The method of claim 7, wherein the temperature is sufficient to form both the polyphosphite compound and one or more members selected from the group consisting of potassium phosphate, potassium polyphosphate, and potassium phosphite.

15. A method of treating a plant for a bacterial or fungal infection, the method comprising applying an effective amount of a fertilizer composition comprising a polyphosphite compound that is individually effective against both fungal and bacterial plant pathogens to the plant.

16. The method of claim 15, wherein the polyphosphite is potassium polyphosphite.

17. The method of claim 16, wherein a concentration of the potassium polyphosphite is approximately 25-75% by weight of the fertilizer composition.

* * * * *